United States Patent [19]

Doyle et al.

[11] Patent Number: 5,011,243

[45] Date of Patent: * Apr. 30, 1991

[54] REFLECTANCE INFRARED MICROSCOPE HAVING HIGH RADIATION THROUGHPUT

[75] Inventors: Walter M. Doyle, Laguna Beach; Norman S. Hughes, San Clemente, both of Calif.

[73] Assignee: Laser Precision Corporation, Irvine, Calif.

[*] Notice: The portion of the term of this patent subsequent to Aug. 1, 2006 has been disclaimed.

[21] Appl. No.: 907,995

[22] Filed: Sep. 16, 1986

[51] Int. Cl.5 .................... G02B 21/06; G02B 21/18; G01N 21/00

[52] U.S. Cl. .................... 350/1.2; 250/330; 250/353; 350/523; 350/620; 356/73

[58] Field of Search ................ 350/1.2, 1.1, 523, 527, 350/505, 511, 526, 620, 525; 250/330, 353; 356/73

[56] References Cited

U.S. PATENT DOCUMENTS

| | | | |
|---|---|---|---|
| 3,411,852 | 11/1968 | Marinozzi, Jr. | 350/620 X |
| 4,594,509 | 6/1986 | Simon et al. | 250/353 X |
| 4,653,880 | 3/1987 | Sting et al. | 350/620 |
| 4,657,357 | 4/1987 | Nishimura et al. | 350/527 X |
| 4,712,912 | 12/1987 | Messerschmidt | 356/73 |
| 4,764,676 | 8/1988 | Doyle | 250/353 |
| 4,786,169 | 11/1988 | Brierley et al. | 356/73 |
| 4,810,077 | 3/1989 | Sting | 350/525 |
| 4,843,242 | 6/1989 | Doyle | 250/330 |
| 4,852,955 | 8/1989 | Doyle et al. | 350/1.2 |
| 4,877,960 | 10/1989 | Messerschmidt et al. | 350/526 |
| 4,878,747 | 11/1989 | Sting et al. | 350/527 |

FOREIGN PATENT DOCUMENTS

| | | | |
|---|---|---|---|
| 56682 | 5/1891 | Fed. Rep. of Germany | 350/523 |
| 899714 | 12/1953 | Fed. Rep. of Germany | 350/523 |
| 915156 | 7/1954 | Fed. Rep. of Germany | 350/523 |
| 3208706 | 11/1982 | Fed. Rep. of Germany | 350/523 |
| 2102149A | 1/1983 | United Kingdom | 350/523 |

OTHER PUBLICATIONS

Bio-Rad Digilab publication, date unknown.
"Low-Cost FTIR Microscopy Units Gain Wider Use in Microanalysis", C&EN, Dec. 9, 1985, p. 15.

Primary Examiner—Scott J. Sugarman
Assistant Examiner—Martin Lerner
Attorney, Agent, or Firm—Thomas J. Plante

[57] ABSTRACT

An infrared microscope is disclosed which provides illumination for reflectance by the sample. This illumination follows a path through the objective toward the sample, and again, after reflection, through the objective toward the detector. The reflectance illumination is directed toward the objective and sample by a fully reflective mirror, which injects approximately half of the interferometer beam into the microscope, and permits substantially all of the reflected beam to reach the detector.

11 Claims, 8 Drawing Sheets

FIG. 1
BACKGROUND

Input beam from spectrometer

FIG. 2
BACKGROUND

FIG. 3
BACKGROUND

FIG. 4
BACKGROUND

FIG. 7
BACKGROUND

REFLECTANCE INFRARED MICROSCOPE HAVING HIGH RADIATION THROUGHPUT

BACKGROUND OF THE INVENTION

This invention relates to infrared (IR) microscopes, i.e., microscopes which provide for sample, or specimen, illumination by infrared radiation, thus permitting spectral analysis of non-visible radiation wavelengths.

More specifically, the problems which need solution concern IR microscopes in the reflectance mode, in which the sample reflects the radiation, as distinguished from IR microscopes in the transmission mode, in which the radiation passes through the sample.

Providing a microscope for IR reflectance measurements presents some unique challenges. The most significant challenge results from the fact that most of the samples of interest are specular (i.e., highly reflecting). It thus is important to illuminate the sample with radiation that is angled appropriately so that the specular component will reach the IR detector. This need should preferably be accomplished with a design that can be easily switched between transmission and reflection operation.

One way to accomplish specular illumination is to illuminate the sample with off-axis radiation and then to tilt the sample an appropriate amount to achieve the desired result. This approach is generally not desirable from the user's viewpoint, since the sample may often be a small particle of contaminant on a specular surface, and thus might be lost from view if tilted out of the horizontal plane.

A second approach employs a semitransparent beamsplitter which is placed in the optical path. This will typically consist of a thin metallic coating on a transparent substrate such as potassium bromide (KBr). Ideally, the beamsplitter would be 50% transmitting and 50% reflecting. However, practical beamsplitters are more typically 40% transmitting, 40% reflecting, and 20% absorbing. In this approach, the collimated beam from the interferometer is diverted so as to eventually be reflected by the beamsplitter toward the microscope objective. The primary deficiency of such a system is the loss of optical power. Typically, about 40% of the incident beam will be reflected by the beamsplitter toward the sample. After reflection from the sample, the beam must pass through the beamsplitter in order to reach the IR detector. For a typical, good quality beamsplitter, only about 40% will be transmitted. The other 60% will either be absorbed or reflected back toward the interferometer. Thus, as previously stated, the total usable signal, even for otherwise perfect optics, will only be 0.4×0.4=0.16 (i.e., 16%) of the incoming optical beam.

SUMMARY OF THE INVENTION

The present invention substitutes a fully reflecting beam-dividing mirror which sends about half of the available IR beam to the sample, and permits the sample-reflected half of the beam to reach the detector. Thus the throughput efficiency is increased from the approximately 16% throughput of the beamsplitter reflectance microscope to approximately 50%.

The present invention also provides symmetrical illumination at the sample, and causes the radiation toward and away from the sample to travel in essentially the same direction, thus conserving specular reflectance of the sample.

In order to obtain these benefits, the beam-dividing mirror (sometimes called the "injection" mirror) which fully reflects half of the beam must be appropriately located. The injection mirror is preferably so located that it directs the beam toward the sample through the same objective which transmits sample-reflected radiation to the detector. Also, the injection mirror should be so located that it is as close to an image plane of the objective back focus, and as far from an image plane of the sample, as is feasible within the design constraints of the instrument. It is preferable to locate the injection mirror in a portion of the optical system in which the radiation is substantially collimated.

In order to prevent spurious radiation from reaching the detector in the reflectance mode, any optical element which shapes or directs the radiation path on its way from the beam-dividing mirror to the sample should be a fully reflecting (mirror) surface, rather than a transparent lens. Use of a transparent lens would unavoidably create rear (first) surface reflection of the incoming radiation, which would mix with the sample-reflected radiation traveling toward the detector.

DETAILED DESCRIPTION OF PREFERRED EMBODIMENT

For a clear understanding of the present invention, it is useful to first review the general aspects of IR microscopy, and the particular problems created by attempts to use such microscopes in the reflectance mode.

Figure 1:
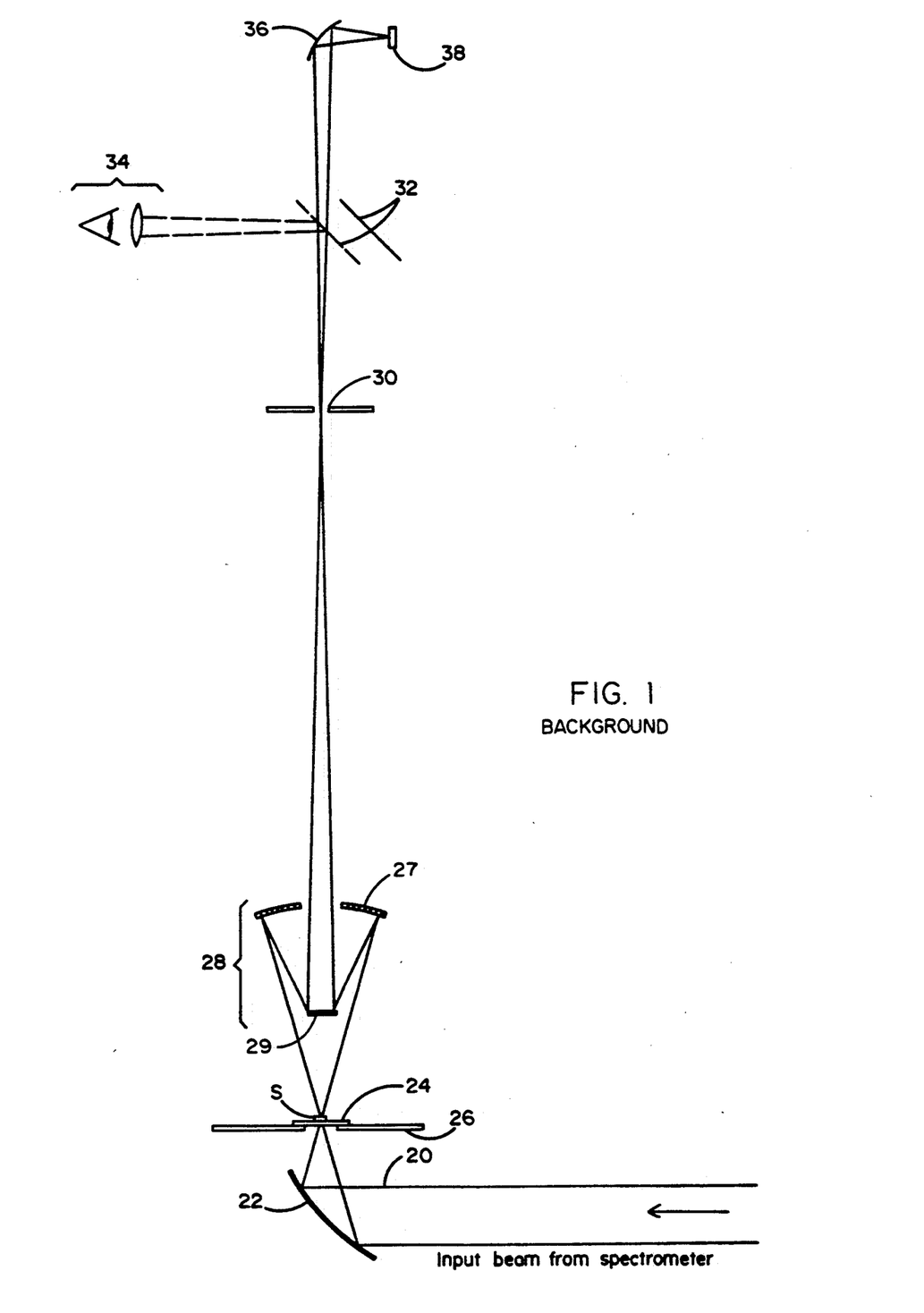
FIG. 1 shows diagrammatically a generalized design of an IR transmission microscope.

FIG. 1 shows diagrammatically a generalized design of an IR transmission microscope. In this illustration, a beam 20 from the interferometer portion of an FTIR spectrometer is focussed onto a sample S by a focussing mirror 22, which is most likely to be a 90 degree off-axis paraboloid. The sample is normally supported on a substrate 24, which is transparent to both visible and infrared radiation (typically a KBr window). The substrate, in turn, is mounted on a microscope stage 26, which is movable along three perpendicular axes.

Radiation transmitted by the sample is collected by a reflecting Cassegrain objective 28 and imaged in a plane containing an adjustable iris, or stop, 30. The Cassegrain 28 comprises a larger concave mirror 27 which collects the rays transmitted through sample S, and a smaller convex mirror 29 which receives the rays reflected from mirror 27 and in turn, because of the angle of incidence, reflects them toward stop 30. For visual sighting, the radiation passing through the stop can be directed by movable mirror 32 to a conventional eyepiece 34. The area of the sample to be studied is selected by moving the stage 24 and adjusting the diameter of the stop 30. Once the adjustments have been made, mirror 32 can be moved out of the beam path, allowing the radiation to be collected by a mirror 36 and focussed on an infrared detector 38. This detector is usually a small area, liquid nitrogen cooled, mercury cadmium telluride (MCT) detector, for maximum sensitivity.

Generally, the visible radiation seen at the eyepiece 34 enters the Cassegrain in the same manner as the IR radiation, i.e., as a collimated beam which is focused by mirror 22. The visible radiation is provided by a separate light source, and may be caused to enter the microscope through a different port from the one receiving the interferometer output beam.

For proper operation, the stop 30 should be accurately positioned in the image plane of the sample, and all elements of the system should be centered on a line defined by the axis of symmetry of the Cassegrain 28. This will optimize the image quality and resolution and insure that the visual center defined by the center of the stop 30 and the center of the eyepiece 34 correspond to the center of the infrared field-of-view of the detector 38.

A Cassegrain is used as the objective lens because it produces a good quality image for both visible and IR radiation over a wide field-of-view, and because it contains no refractive optical elements. The other focusing mirrors in the system are off-axis paraboloids having a much lower cost. Since these paraboloids are used primarily for the IR beam, their imaging characteristics for off-axis rays are not important.

Figure 2:
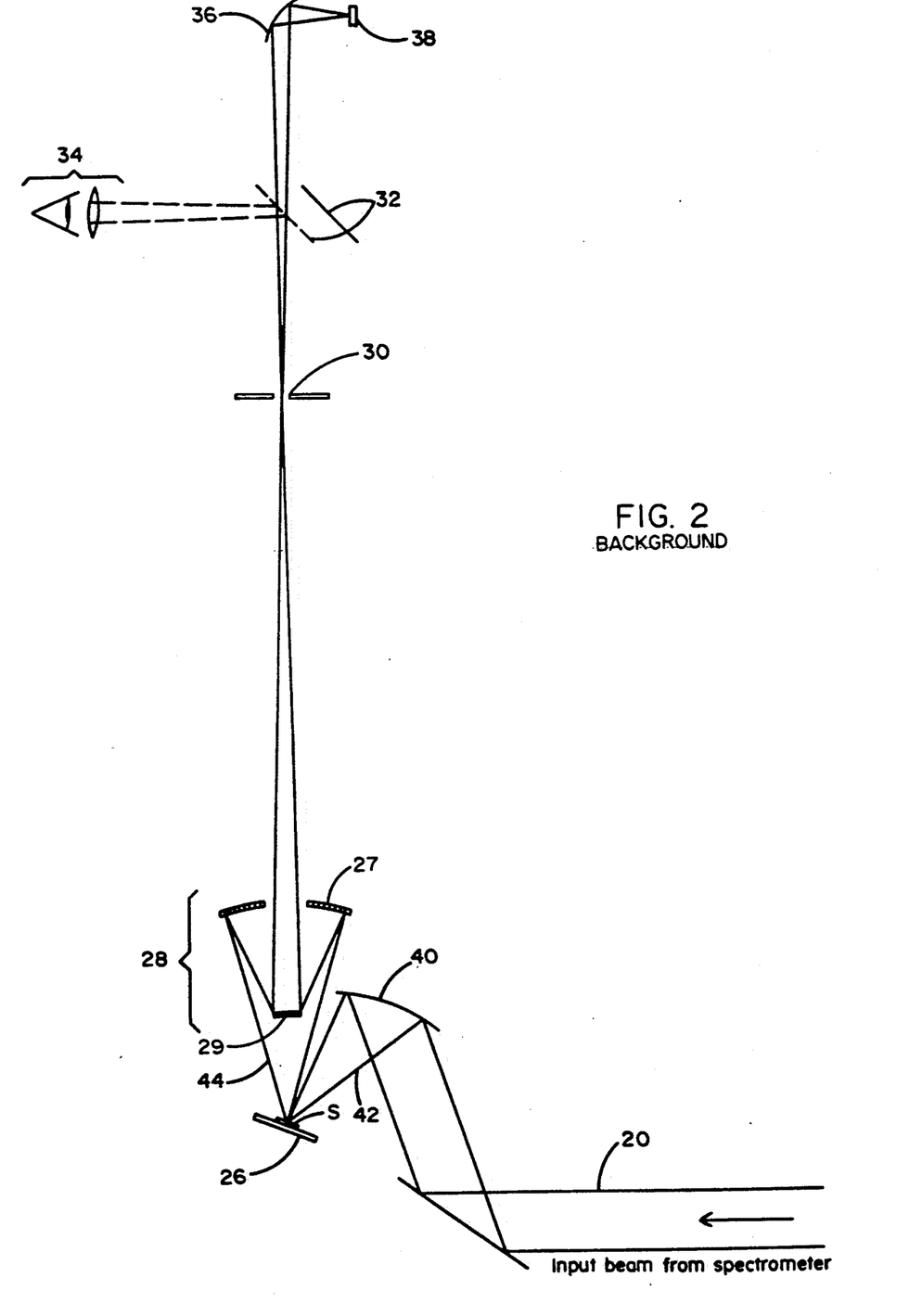
FIGS. 2 and 3 show diagrammatically two different versions of generally inadequate efforts to solve the problem addressed by the present invention.

FIG. 2 illustrates one of the generally inadequate efforts to add a reflectance capability to the IR microscope of FIG. 1. In this illustration, the sample S is tilted, as shown, by tilting its stage 26. The incoming collimated IR beam 20 is focused by a parabolic reflector 40 on the sample. The directions of the rays in focusing beam 42 are separated from the directions of rays in beam 44 which enters the Cassegrain. As previously explained, the tilting of the sample might remove it from the focal point of the reflected beam; and the lack of radiation perpendicular to the sample tends to diminish the specular reflection entering the Cassegrain.

Figure 3:
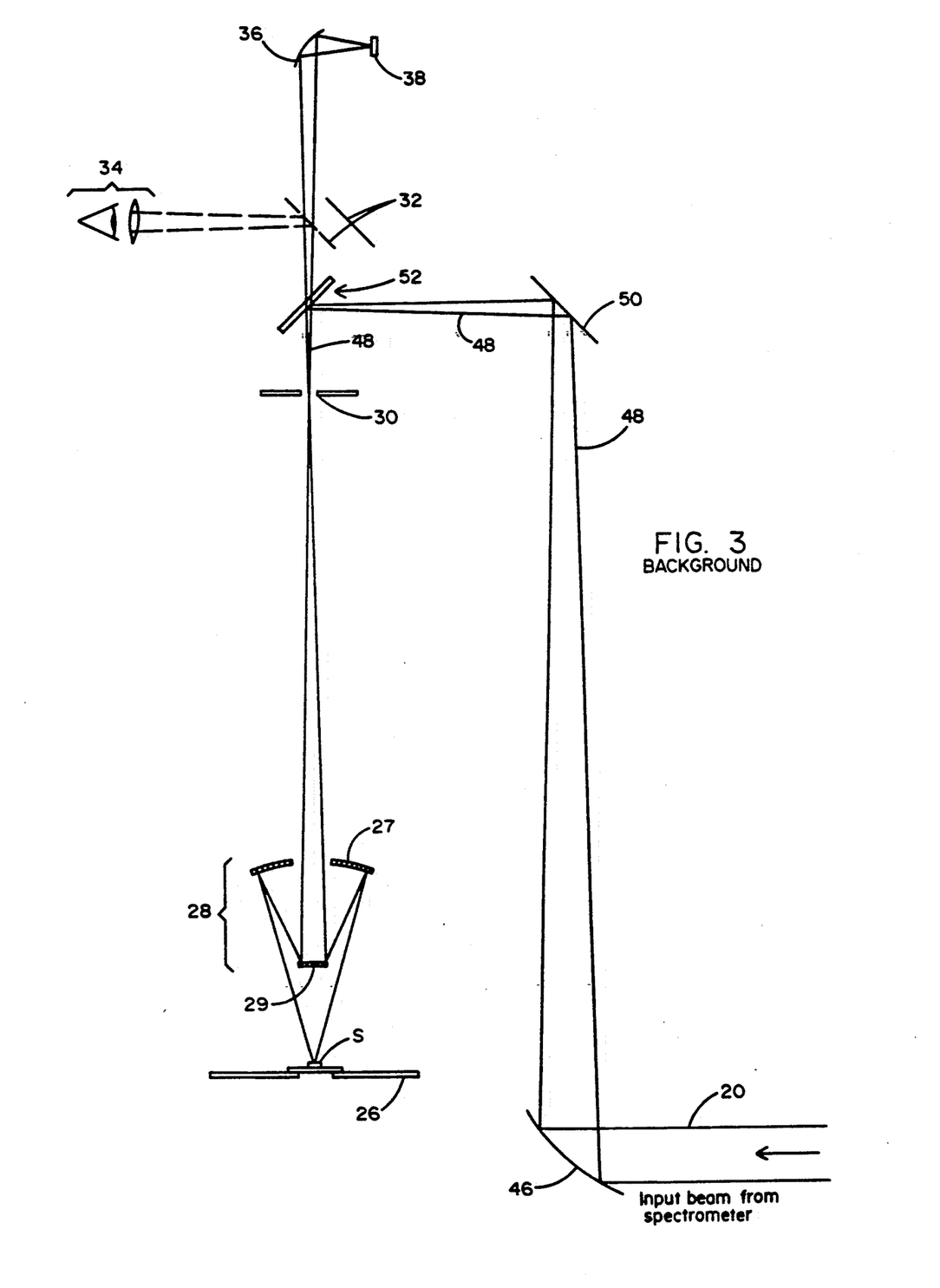

FIG. 3 illustrates another of the generally inadequate efforts to add a reflectance capability to the IR microscope of FIG. 1. In this illustration, the incoming collimated IR beam 20 is diverted from the normal path of the transmission mode by a long focal length parabolic reflector 46, which sends a narrowing beam 48 to a flat 45° mirror 50. Mirror 50, in turn, reflects the narrowing beam 48 toward a beamsplitter 52. The focal length of paraboloid 46, and the positions of the other optical elements, are chosen to cause the incident beam 48 to come to focus in the plane of stop 30. It is also important that the incident beam 48 be so directed that, after reflection by beamsplitter 52, it is coaxial with the microscope optics and has a divergence approximately equal to the angular spread indicated by the rays shown between stop 30 and Cassegrain 28. In other words, the optimum condition occurs when the incoming beam is the mirror image of the optical beam normally used in transmission.

The primary deficiency of the FIG. 3 system is the loss of optical power caused by beamsplitter 52. As previously stated, about 40% of the incident beam will be reflected by the beamsplitter toward the sample S. After reflection from the sample, the beam must pass through the beamsplitter 52 in order to reach the IR detector 38. For a typical, good quality beamsplitter, only about 40% will be transmitted. The other 60% will either be absorbed or reflected back toward the interferometer. Thus, as previously stated, the total usable signal, even for otherwise perfect optics, will only be about 16% of the incoming optical beam.

The present invention is concerned with the injection of incident IR radiation into the microscope optical train, not by a semitransparent beamsplitter, but by a fully reflecting (approximately 100%) mirror so placed as to maximize the transfer of optical power from the interferometer to the sample and from the sample to the detector.

To understand the nature of the invention, it is useful to first consider a case that does not work, i.e., the case in which the signal is injected by a 100% mirror in or near the plane of stop 30. Consider FIG. 4, which illustrates the transfer properties of a simple lens 53. As in the microscope case, assume that the lens is being used to produce an enlarged image of a sample S which is on a specularly reflecting substrate. The image will be formed in a plane 54, which is analogous to the plane of stop 30 of the microscope.

Figure 4:
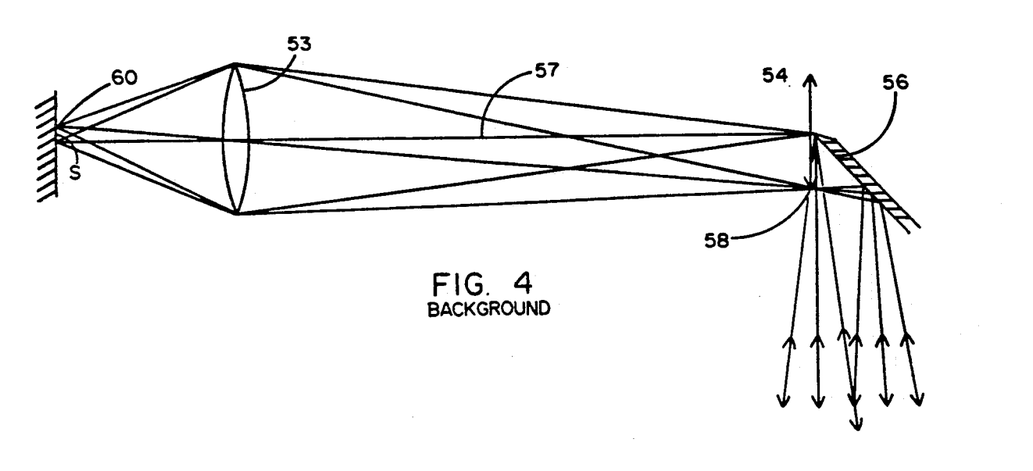
FIGS. 4, 5 and 6 are diagrammatic illustrations of the applicable optical theory as applied to optical systems incorporating lenses as focusing elements, instead of reflecting optics.

Assume that the IR signal is entered into the system by means of a 100% reflecting mirror 56 which is located immediately behind the sample image plane 54, and which blocks the lower half of the optical field in this plane. As in the case of the semitransparent beamsplitter, the incoming radiation will be configured to approximate a mirror image of the normal transmission optical path.

It can be seen from FIG. 4 that all of the radiation injected by mirror 56 will fall above the system axis indicated by ray 57 in the sample plane. For example, all of the radiation passing through the point 58 in the sample image plane 54 will be imaged at point 60 in the sample plane. Since the optical paths are reversible, this radiation at point 60, after reflection from the sample substrate, will return to point 58, and be reflected back out of the system by mirror 56. Virtually no radiation will pass through the upper half of the sample image plane 54 in such a way as to reach the detector.

Figure 5:
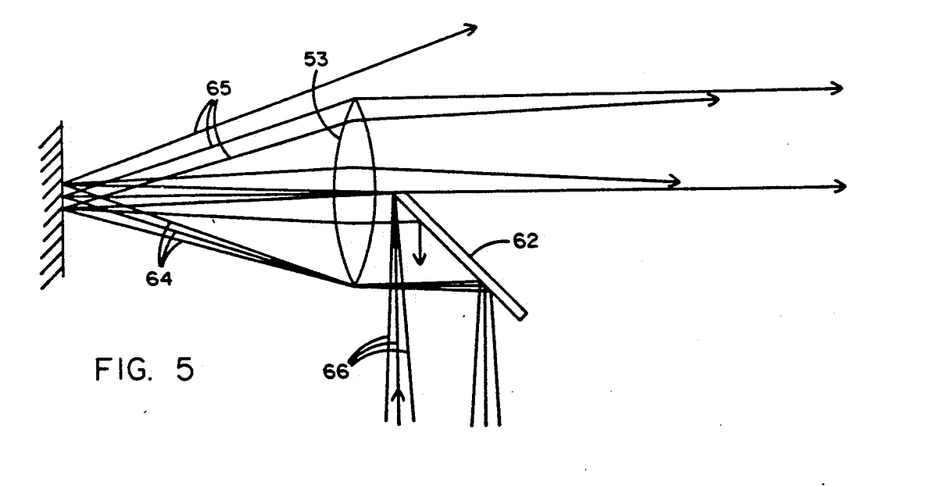

The situation is entirely different if the IR radiation is injected in the vicinity of the lens 53, rather than the sample image plane 54. This condition is shown in FIG. 5. A 100% mirror 62, which is located in the vicinity of lens 53, blocks the lower half of the optical field. Each area of the lens 53 will collect radiation from every part of the sample. Similarly, if the sample is illuminated through the lens, then each area of the sample will receive radiation from each area of the lens. Thus, if only half of the lens is used to illuminate the sample, the sample will be approximately uniformly illuminated, but at one half intensity. If the specular substrate is normal to the axis of the optical system, the radiation, e.g., rays 64, which enters through the lower half of the lens will be reflected to the upper half of the lens and will be free to pass on to the IR detector, e.g., rays 65.

A study of FIG. 5 reveals that there are two limitations to the total amount of radiation power that can be transmitted by the design illustrated. First, the outer edge of the lens 53 acts as an aperture stop both for incoming and for outgoing radiation. The rays indicated by 64 are the marginal incoming rays allowed by the lens aperture. As the figure illustrates, after reflection, not all of these rays (65) will fall within the exit aperture formed by the opposite edge of the lens. This is an inherent limitation of all reflectance microscopes, regardless of the method used for injecting the IR beam.

The second limitation relates to the fact that the inner edge of the injecting mirror 62 also acts as a stop. The bundle of rays indicated by 66 represents the limiting incoming rays that will be reflected by the injecting mirror into the lens 53 and to the sample. After being reflected by the sample, these rays continue to diverge until they again reach the lens, at which point they will have spread to about twice the diameter of the illuminated spot on the sample. Since the injection mirror 62 is immediately behind the lens, only about half of the marginal rays will be able to get past this mirror after reflection. The others will be intercepted by the mirror 62 and reflected out of the desired path.

The above limitation will not be severe as long as the area of the illuminated spot on the sample is small compared to the total beam area in the vicinity of the injection mirror (i.e., the lens diameter in this case). However, it is still useful to specify the ideal condition. This is illustrated by FIG. 6.

Figure 6:
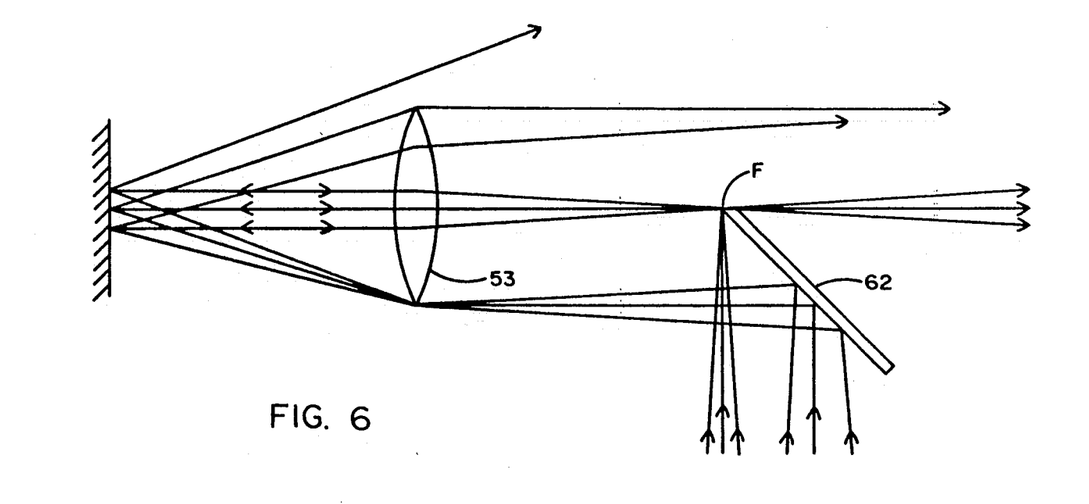

In FIG. 6, the inner edge of the injection mirror 62 is at a back focal point of the lens (i.e., a distance to the right of the lens equal to the focal length). The marginal bundle of rays reflected from this edge will thus be diverging from the focal point when they strike the lens. As a result they will form a collimated beam after passing through the lens. As long as the reflective substrate (at the sample) is perpendicular to the beam path, this collimated beam will be refocused to the original point of origin at the edge of the injection mirror 62. It is clear that a bundle of rays reflected toward the lens from a point slightly below the focal point will be able to pass freely just above the edge of the mirror 62.

The key element of the example shown in FIG. 6 is the fact that the injection mirror 62 is positioned so that its inner edge is reimaged back on itself, after reflection from the sample substrate. Any other position in the optical system which shares this characteristic will also be appropriate.

It can be seen that the approach illustrated in FIG. 6 achieves two desired results: The sample is uniformly illuminated, and the overall signal transfer efficiency can approach a theoretical maximum of 50%, compared to the signal obtained using the same optics in transmission. This compares favorably with typical efficiencies of 16% for the semitransparent beamsplitter.

Figure 7:
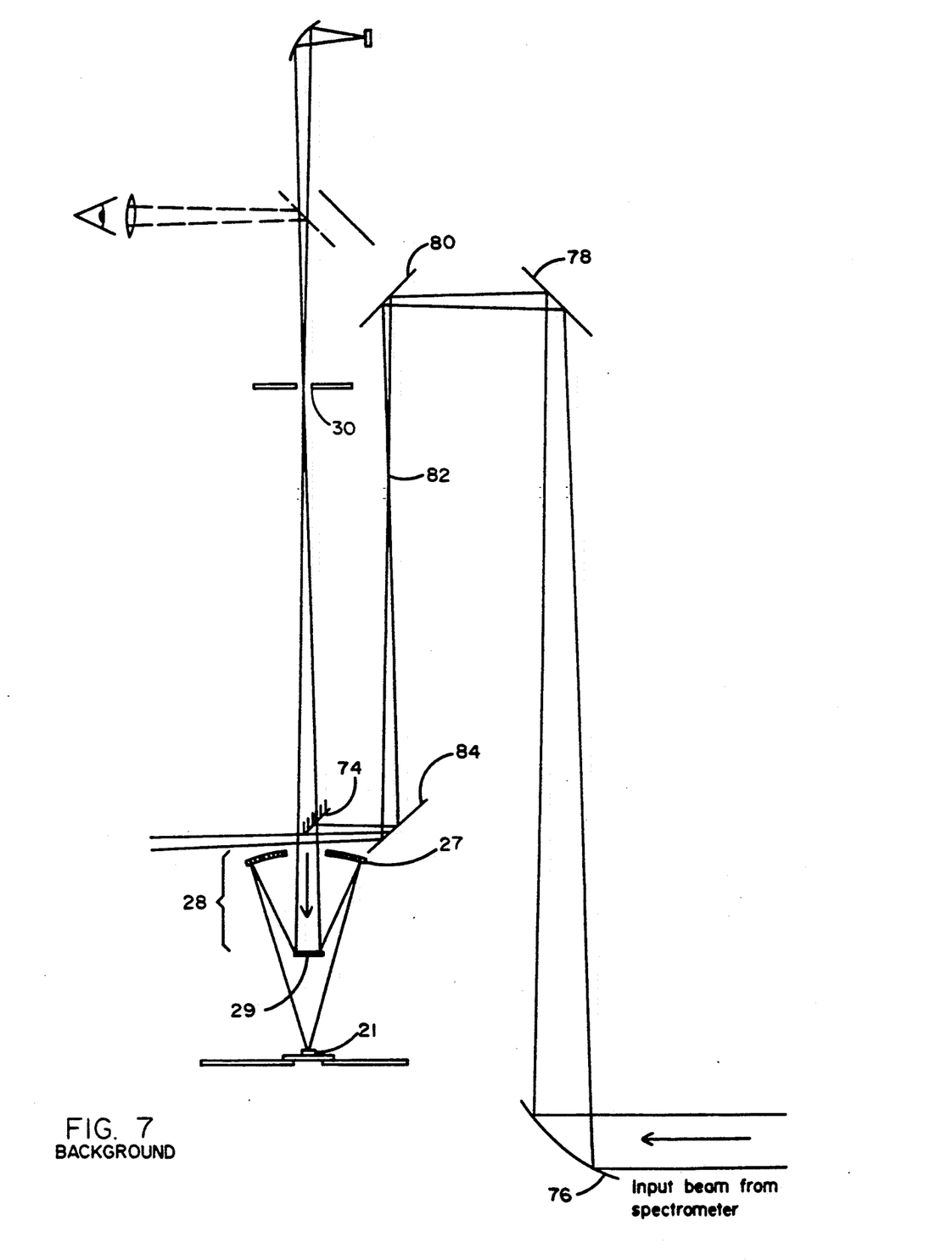
FIG. 7 shows diagrammatically the problems involved in certain methods of applying the theory illustrated in FIGS. 4-6 to the optical system of an IR microscope.

Returning to consider the actual microscope optics, note that FIG. 7 illustrates a design in which the injection mirror 74 is placed in the vicinity of the back focus of the Cassegrain 28. While this position might be acceptable for some designs, it turns out to be inconvenient for others. In particular, in order to provide an input beam configuration which is a mirror image of the microscope internal beam, it is necessary to provide a fairly long optical path, as shown in FIG. 7. A long focal length off-axis paraboloid 76 and two flat mirrors (78 and 80) are used to bring the beam to a focus at point 82. The radiation diverging from this point strikes mirror 84 and is directed to the injection mirror 74. It can be seen that 82 is a mirror image of 30, and that the input beam has the same divergence as the normal microscope optical path between 30 and the Cassegrain.

Figure 8:
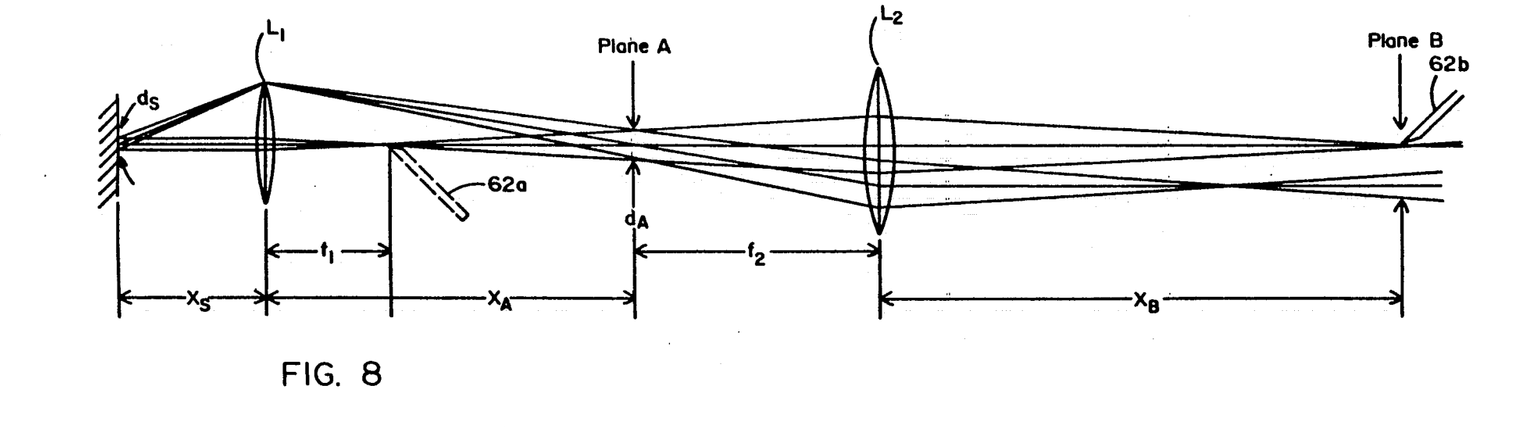
FIG. 8 shows diagrammatically a practical means of applying the relevant theory to an optical system having a focusing lens and a collimating lens.

In designing a practical microscope, it may not be convenient to inject the IR beam in the vicinity of the Cassegrain back focus. An alternative is to inject it in the vicinity of an image of the Cassegrain back focus. To understand this, again consider the lens analogy (FIG. 8). If the illuminated area on the sample is assumed to have a diameter d(S), the objective lens L1 will produce a magnified image in plane A having a diameter d(A). Now consider a second lens L2, positioned a distance f(2) beyond the plane A, where f(2) is the focal length of L2. This lens will thus produce an image of the sample located at infinity (i.e., a point source in either the sample plane or plane A would give rise to a collimated beam out of L2).

In FIG. 8, the dashed mirror 62a indicates the optimum position for the injection mirror, if it is to be placed at the back focus to the objective lens. This position has an image 62b in plane B, which image is formed by lens L2. The location of plane B can be easily determined by use of the simple lens formula. An injection mirror located in plane B will give comparable results to one positioned at the back focus of the objective lens.

In many cases it will not be convenient to place the injection mirror in plane B, since this may entail excessive path length. However, it can be seen that reasonably good results will be obtained if the injection mirror is located anyplace after the collimating lens L2. In this case, the system efficiency will approach the ideal of 50% as the size of the illuminated sample approaches zero. For finite samples the amount of signal loss will be roughly proportional to the ratio between the beam spread at the position of the injection mirror caused by the finite size of the sample and the diameter of the beam at this point corresponding to a point source.

Figure 9:
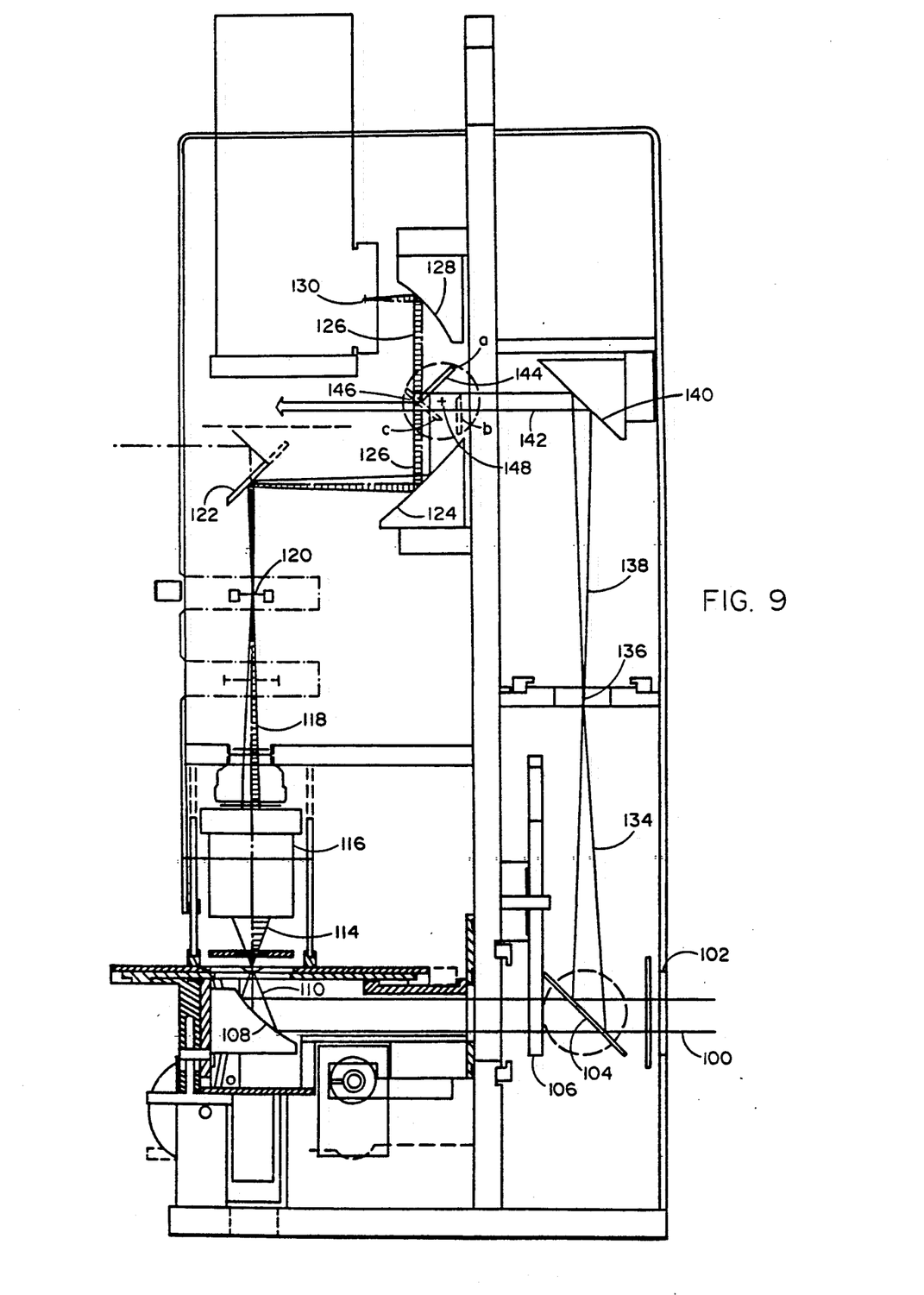
FIG. 9 shows a microscope incorporating the concepts of FIG. 8 to the extent practicable in an instrument having dimensional constraints.

A preferred embodiment of the invention is represented by the optical design of the microscope illustrated in FIG. 9. In the transmission mode, the operation of this microscope generally follows the description given with regard to FIG. 1. A collimated IR beam 100 from the interferometer enters the microscope through a port 102. A parabolic mirror 104, seen in the figure, is not in position to intercept beam 100 in the transmission mode. It is one of several reflectors carried by a mirror wheel 106, which functions as an optical switch. Mirror wheel 106 is disclosed in detail in common assignee application U.S. application Ser. No. 907,993, filed Sept. 16, 1986, now Pat. No. 4,852,955.

For the transmission mode of the microscope, wheel 106 is rotated to a position in which it permits beam 100 to pass through to a short focal length parabolic mirror 108, which causes its reflected radiation 110 to focus at the location of the sample. The diverging, post sample radiation 114 enters the Cassegrain objective 116; and beam 118 leaving the Cassegrain focuses at sample image plane 120. After passing through the sample image plane 120, the IR radiation is reflected by movable mirror 122, which directs it to a 90 degree off-axis paraboloid 124. Mirror 124 is so positioned that its focus falls in the center of the stop (in plane 120). It thus collects the radiation diverging from focal plane 120 and forms a beam 126 which is nominally collimated (i.e., approaching a pure collimated condition as the stop is closed down). This beam is then directed to a short focal length paraboloid 128 which focusses it on an IR detector 130.

For the reflectance mode of the microscope, mirror wheel 106 is rotated to a position in which parabolic mirror 104, carried by the wheel, and having a relatively long focal length, directs the IR radiation 134 along a path parallel to radiation 118. Radiation 134 focuses at 136, and the diverging beam 138 is reflected by a parabolic mirror 140, which has a relatively long focal length, and which forms a collimated beam 142.

Beam 142 is interrupted by an injection mirror 144, which is positioned to intersect one half of the beam 142 (i.e., its inner edge 146 is positioned as closely as possible to the center of beam 142). Since beam 142 is collimated, the ideal form for the injected beam is also collimated. This configuration is established by means of the confocal paraboloids 104 and 140.

Figure 11:
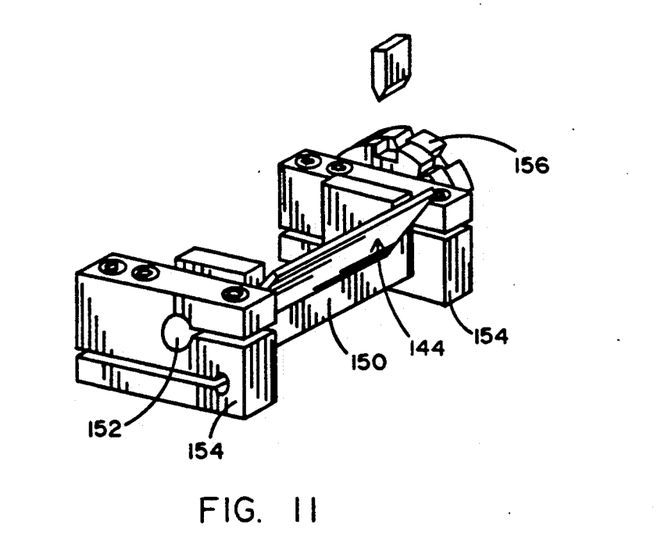

Beam injection mirror 144 is mounted excentrically on a rotating mechanism with its center of rotation at the point marked 148. This allows the microscope to be switched between three different modes of operation with a simple rotary motion. In position "a" (solid), mirror 144 is positioned for reflectance operation, as discussed above. In position "b", mirror 144 does not interrupt the microscope optical path. In this case the microscope can be used in the conventional transmission mode by also switching mirror 104 out of the beam path. In position "c", mirror 144 intersects all of the optical path. If mirror 104 is then switched into the beam path, the full IR beam will be diverted past the microscope optics and directly to detector 130, after going through a focus at 136. This focal region provides a convenient place to mount large area samples for conventional macroscopic analysis. A sample holder mounted in this region can also be advantageous in reflectance operation as a place to mount apertures, polarizers, or other types of filters. FIG. 11 shows the support mechanism for mirror 144. The mirror is carried by a holder 150, which is rotated around a center defined by pivot pins 152 secured to the holder. The pivot pins rotate in openings in two stationary vertical members 154. A cog wheel 156 is used to rotate the pivot pins and reposition mirror 144.

The 50% of collimated beam 142 which is reflected by mirror 144 will be reflected by parabolic mirror 124 and flat mirror 122, focussing at stop 120. The beam will then diverge and enter Cassegrain 116, which will focus it at sample 112 for reflectance by the sample. The sample-reflected radiation will return through Cassegrain 116, and through focal plane stop 120. It will then be reflected by flat mirror 122 toward parabolic mirror 124. The latter will reflect the beam in such a way that it is not intercepted by injection mirror 144 and, therefore, it will reach detector 130 (after being focused by parabolic mirror 128).

The optical effect of reflecting half of the IR radiation toward the sample leads to a 50% reduction of illumination at the sample, but does not cause reduction of the scene, or field, which is illuminated. In other words, there is uniform illumination at the sample, not localization of illumination. By fully reflecting half of the sample-illuminating radiation, rather than using a beamsplitter, the effective throughput is greatly enhanced. Another advantage of the fully reflecting beam-dividing mirror over a beamsplitter is that a beamsplitter is inherently frequency sensitive, whereas the fully reflecting mirror is not. Also, directing the reflectance radiation through the microscope aperture provides a beam which creates maximum reflectance information at the detector.

Figure 10:
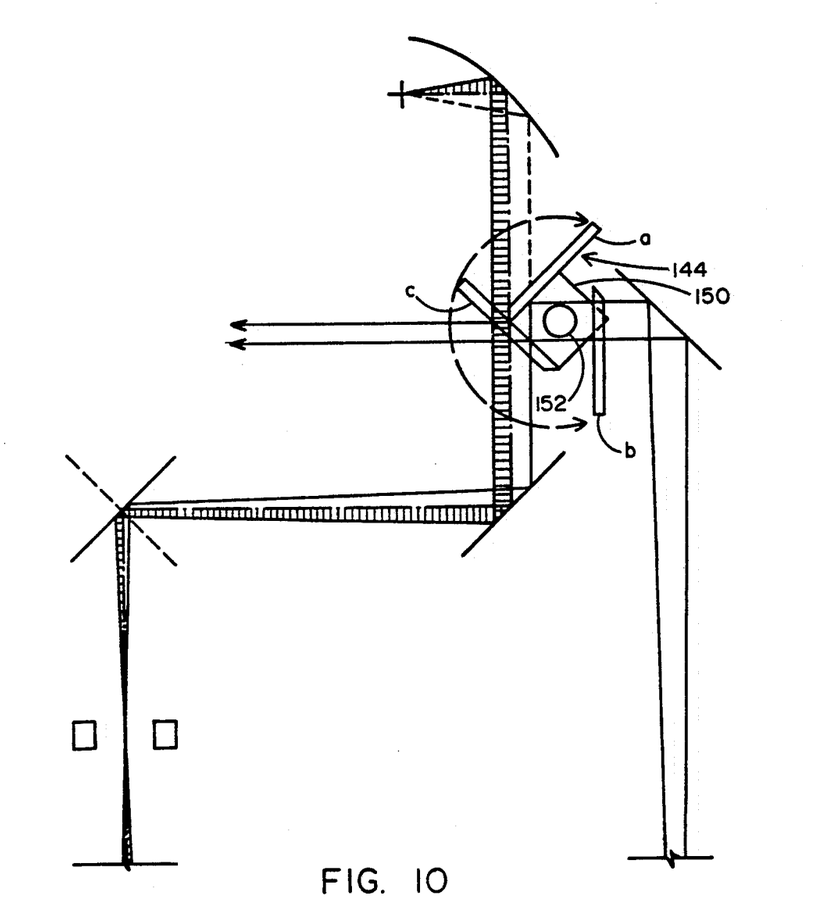
FIGS. 10 and 11 show the three-position injection mirror in side, and isometric, views, respectively.

FIG. 10 is an enlarged view of the reflectance injection mirror, and of the radiation paths when the microscope is in the reflectance mode. Other radiation paths are omitted. In FIG. 9, the radiation reflected by injection mirror 144 through the Cassegrain onto the sample is distinguished from the radiation reflected back by the sample through the Cassegrain to detector 130 by shading the latter, and not shading the former.

In comparing the optical elements in the microscope of FIG. 9 with the optical elements in the lens system of FIG. 8, it should be noted that the collimating paraboloid 124 of FIG. 9 performs the same function as the collimating lens L2 of FIG. 8. Also, the effective aperture, which is the smaller Cassegrain mirror in FIG. 9, corresponds functionally to the lens L1 of FIG. 8. In the discussion of FIG. 8, it was explained that the ideal location of the injection mirror would be in Plane B, which is the image plane of lens L1. By analogy, the ideal location of injection mirror 144 in FIG. 9 would be in the image plane of the small Cassegrain mirror.

Design limitations based on available space do not permit this ideal location of mirror 144 in FIG. 9. Calculations will show that the image plane of the throughput-limiting aperture in FIG. 9 would be several inches farther from paraboloid 124 than the actual location of mirror 144. However, because mirror 144 is in a portion of the radiation path which is substantially collimated, the inability to use the ideal location has not, in practice, caused significant reduction of efficiency.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In an optical instrument having a sample supported in the instrument, a fully-reflecting objective, means for observing visible radiation at the sample location, a detector of infrared radiation, and means for causing a post-interferometer infrared radiation beam to enter the instrument, an infrared optical system combining transmission mode and reflectance mode functions, comprising:

transmission mode means for directing the post-interferometer radiation beam into and completely through the objective from one direction for transmission illumination of the sample;

reflectance mode means for directing the post-interferometer infrared radiation beam into and completely through the objective from the opposite direction for reflectance illumination of the sample;

the reflectance mode means including a beamsplitter which (a) incorporates a fully reflecting mirror, (b) is located at a distance from the objective, and (c) causes approximately half of the interferometer infrared radiation beam to pass through the objective to be reflected by the sample; and means for directing substantially an entire sample-reflected radiation to the detector.

2. The optical instrument of claim 1 in which the mirror is so located that it directs the reflected half of the incoming radiation toward the objective, allows the unreflected half of the incoming radiation to follow an exiting path, and allows the path of the sample-reflected radiation to pass across its edge as the radiation travels to the detector along a path which crosses laterally the radiation exiting path.

3. The optical instrument of claim 1 in which the radiation beam at the beamsplitter has the cross-sectional size of a substantially collimated beam.

4. An infrared microscope operable in either a transmission mode or a reflectance mode, comprising:
a source of infrared radiation which supplies a beam entering the microscope;
means for supporting a sample in a position to be illuminated by the infrared radiation in either the transmission mode or the reflectance mode;
a detector which receives radiation after it has illuminated the sample;
an all-reflecting microscope objective whose optical elements are mirrors, and whose location is such that (a) post-sample radiation passes through the objective in the transmission mode, and (b) both pre-sample radiation and post-sample radiation pass through the objective in the reflectance mode;
a first focusing reflector which directs source-provided radiation to the sample in the transmission mode;
a second focusing reflector which, in the reflectance mode, directs source-provided converging radiation through the objective to focus at the sample, and receives post-sample diverging radiation from the objective and directs it toward the detector;
means for directing substantially collimated source-supplied radiation toward the second focusing reflector in the reflectance mode; and
a fully-reflecting flat beam-dividing mirror which, in the reflectance mode, causes approximately half of such collimated radiation to be reflected by the second focusing reflector toward the sample, and permits substantially the entire post-sample radiation to travel from the second focusing reflector to the detector.

5. The infrared microscope of claim 4 in which the objective comprises:
a relatively large area mirror which (a) has a central aperture, (b) has its focal point at the sample, (c) reflects only post-sample radiation in the transmission mode, and (d) reflects both pre-sample and post-sample radiation in the reflectance mode; and
a relatively small area mirror which (a) reflects radiation passing through the aperture in the larger Cassegrain mirror, such radiation having a focal point between the sample and the detector, (b) reflects radiation coming from a larger Cassegrain mirror in the transmission mode, and (c) both reflects radiation toward, and reflects radiation from, the larger Cassegrain mirror in the reflectance mode.

6. The infrared microscope of claim 4 which also comprises:
two confocal parabolic reflectors;
one of which receives the source-provided radiation and provides a converging beam traveling toward a focal point; and
the other of which receives a diverging beam traveling from said focal point and reflects it as a collimated beam to the flat beam-dividing mirror.

7. In a microscope having a sample located by a supporting member, a fully-reflecting microscope objective, means for observing visible radiation at a sample location, a detector of infrared radiation, and means for causing a post-interferometer infrared radiation beam to enter the microscope, an infrared optical system combining transmission mode and reflectance mode functions, comprising:
transmission mode means for directing an entering infrared radiation beam into the objective from one direction for transmission illumination of the sample;
reflectance mode means for directing the entering infrared radiation beam into the objective from the opposite direction for reflectance illumination of the sample;
the reflectance mode means including a beamsplitter which incorporates a fully reflecting mirror and which intersects half of the entering beam so as to cause half of the entering beam to pass to the sample for reflectance; and
the reflectance mode means including means for causing half of the entering beam to travel through one half of the objective, then to illuminate the sample, and then to return through the other half of the objective to illuminate the detector.

8. The microscope of claim 7 in which the radiation beam intersected by the beamsplitter has the cross-sectional size of a substantially collimated beam.

9. In a microscope having a sample supported therein, a detector of infrared radiation, and means for causing a post-interferometer infrared radiation beam to enter the microscope, an infrared optical system combining transmission mode and reflectance mode functions, comprising:
transmission mode means for causing the post-interferometer radiation beam to provide transmission illumination of the sample;
reflectance mode means for causing the post-interferometer infrared radiation beam to provide reflectance illumination of the sample;
the reflectance mode means including:
(a) a sample image plane at a distance from the sample at which plane the radiation beam focuses before and after illuminating the sample; and
(b) a beam divider which receives the radiation beam at a distance ahead of the sample image plane, and which causes half of the radiation beam to be removed from the optical system and the remaining half of the radiation beam to illuminate the sample and then pass to the detector without further obstruction by the beam divider.

10. The microscope of claim 9 in which the beam divider is a mirror whose edge extends across the center of the radiation beam cross-section.

11. The microscope of claim 9 in which:
the transmission mode means causes substantially the entire radiation beam to provide transmission illumination of the sample and thereafter travel to the detector without obstruction by the beam divider.

* * * * *